United States Patent [19]

Silberman

[11] Patent Number: 5,198,366
[45] Date of Patent: Mar. 30, 1993

[54] METHOD FOR THE DETECTION OF PREGNANCY DISORDERS

[75] Inventor: Michael Silberman, P.O. Box 9697, Haifa 31096, Israel

[73] Assignees: Technion Research & Development Foundation Ltd.; Michael Silberman, both of Haifa, Israel

[21] Appl. No.: 745,894

[22] Filed: Aug. 16, 1991

Related U.S. Application Data

[63] Continuation-in-part of Ser. No. 603,232, Oct. 25, 1990, abandoned, which is a continuation-in-part of Ser. No. 24,023, Mar. 10, 1987, abandoned.

[30] Foreign Application Priority Data

Mar. 23, 1986 [IL] Israel .......................................... 78237

[51] Int. Cl.$^5$ ............................................. G01N 33/68
[52] U.S. Cl. .......................................... 436/86; 436/65; 436/87; 436/503; 436/504; 436/510
[58] Field of Search ...................... 436/65, 86, 87, 504, 436/503, 510

[56] References Cited

U.S. PATENT DOCUMENTS 4,500,451 2/1985 Bohn et al. .

*Primary Examiner*—Sam Rosen
*Attorney, Agent, or Firm*—Foley & Lardner

[57] ABSTRACT

The present invention relates to a method for an early stage detection of three specific pregnancy-related disorders: preeclampsia, intrauterine growth retardation and preterm delivery. According to the method, an antigen consisting of a specific human-derived placental soluble protein, known as PP-13, is determined by radioimmunoassay or ELISA. In the radioimmunoassay method, the PP-13 is labelled by a radioactive iodine and the bounded iodine is counted and correlated with standard curves. The best results are obtained when the protein to be labelled by radioactive iodine is present at a concentration of above 0.71 mg/ml. In case of the ELISA method, the quantitative determination of PP-13 is carried out with an alkaline phosphatase substrate and measured at an optical density of 405 nm.

13 Claims, 3 Drawing Sheets

METHOD FOR THE DETECTION OF PREGNANCY DISORDERS

This application is a continuation in part of U.S. Pat. application Ser. No. 07/603,232 filed Oct. 25, 1990, which was a continuation in part of U.S. Pat. application Ser. No. 024,023 filed Mar. 10, 1987 both now abandoned.

The present invention relates to a new method for the detection of pregnancy-related disorders. More particularly, the invention relates to a new method for the detection of three specific pregnancy-associated disorders: severe preeclampsia, Intra-Uterine Growth Retardation (IUGR) and preterm delivery, at a relatively early stage of pregnancy.

BACKGROUND OF THE INVENTION

As known, high risk pregnancies constitute about 10 to 25% of pregnancies. Among the high risk pregnancy disorders the following can be mentioned: diabetes, kidney diseases (such as chronic pyelonephritis, chronic pyelonephritis and renal insufficiency), heart diseases (such as primary pulmonary and hypertension).The known methods for controlling the progress of pregnancy, have the disadvantage of detecting the status of pregnancy disorders at a relatively late stage, when the clinical signs and symptoms are already apparent.

There are several hormone assays suggested to give an indication whether placental function is normal or to predict impending fetal death. The tests most widely used are: urine estriol, urine total estrogens, serum unconjugated estriol and serum placental lactogen. As known, estriol is an estrogenic compound produced by the placental from precursors derived from fetal adrenal cortex and fetal liver. The conjugated form of estriol is excreted into the maternal urine. Serum estriol can be measured either as total estriol or as unconjugated estriol. It usually is measured as unconjugated estriol in order to exclude maternal contribution to the conjugated fraction. Urine estriol can be measured as total estriol or as total estrogens, since estriol normally constitutes about 90% of urine total estrogens.

Estriol can be detected by immunoassay as early as the ninth week of gestation. Therefore, estriol values slowly but steadily increase until the last trimester, when there is a more pronounced increase. Clinical use of estriol measurement is based on the fact that severe acute abnormality of the fetoplacental unit, such as a dead or dying placenta, is manifested either by failure of the estriol level to continue rising or by a sudden marked and sustained decrease in the estriol level. A recent report (M.Scharf et.al. J.Obstet.Gynec.reprod. Biol., 17:365-75, 1984) concludes that in view of the low correlation between patients with abnormal serum free estriol as the antepartum pathological test, the estriol measurement can not be considered a reliable predicting tool to estimate the actual pregnancy outcome.

Urine total estrogen was the first test used, since total estrogen can be assayed by standard clinical techniques. However, urine glucose falsely increases the results and certain other substances such as urobilinogen also may interfere. On the other hand, maternal hypertension, preeclampsia, severe anemia and impaired renal function can decrease considerably urine estrogen or estriol secretion. Decrease in the level may also occur to a variable degree in a number of fetuses with severe congenital anomalies. It was also reported that continued bed-rest to the pregnant woman caused an increase in the estriol excretion values of about 20 to 30% over the levels determined from ambulatory persons. Because of the problems associated with collection of urine or serum estriol specimens and interpretation of the values, as well as the disturbing number of false positive and negative test results, most of the clinical people refrain from correlating these measurements with placental disorders. Moreover, all the previous methods did not reveal the pregnancy disorders at an early stage of their initiation, but only when the particular disease was already apparent.

It is an object of the present invention to provide a, simple method for the detection of pregnancy disorders at an early stage. It is an another object of the present invention, to provide a simple method for the detection of pregnancy disorders that has a high sensitivity. It is yet another object of the present invention to provide a simple method for the detection of pregnancy disorders, said method being not influenced by other extraneous factors related thereto.

SUMMARY OF THE INVENTION

The invention is based on antigenic compounds released from the placental tissue into body fluids and uses a particular protein specific to human placenta, known as PP-13, which can be subsequently determined by the ELISA or radioimmunoassay methods.

The PP-13 is characterized by the following physicochemical properties:
  isoelectric point, in the range of between 4.6 to 4,9;
  molecular weight, below 35,000 daltons;
  carbohydrate content, below 1%, and
  electrophoretic mobility, in the range specific to albumin.

It was surprisingly found that using one of the above methods with the particular protein, it is possible to establish an early detection of three pregnancy related disorders in pregnant woman: severe preeclampsia, IUGR and preterm delivery. This is in contrast to known prior tests claiming to determine the pregnancy disorders only after their existence in an advanced stage of placental illness. The soluble protein PP-13, found to be suitable for the present invention, was discovered in the last few years and is described in the U.S. Pat. number 4,500,451 (H.Bohn et al). It is mentioned therein that an envisaged use for this protein could be for the diagnostic purpose of tumors detection of trophoblastic character, although no data or actual Examples were presented. It should be pointed out, that the above three pregnancy-related disorders have nothing to do with tumors. Moreover, this reference does not suggest of any correlation between the PP-13 protein and risk of placental damage which would cause pregnancy disorders, and therefore could not determine whether any placental damage has occurred. The discovery according to the present invention, to utilize the placental protein PP-13, for the prediction of occurence of preeclampsia, IUGR and preterm delivery is quite surprising, in view of prior art statements which discuss various placental proteins, stipulating that they are of no value for this purpose Thus, for instance in a paper by J.G. Westergaard (British Journal of Obstetrics and Gynaecology, December, 1984, Vol. 91, page 1224) it is stipulated:

"These data suggest that the measurement of the placental proteins examined here is of no value in the prediction of occurence of pregnancy-related hypertension."

The Inventor carried out a number of experiments with various placental proteins and found that there are many placental proteins which are indeed not suitable for the present invention although they possess one or two of their physico-chemical properties quite similar to those of PP-13. Thus for instance PP-4, which was found to be unsuitable, has a molecular weight of 35,000 (i.e. similar to the PP-13) but its carbohydrate content is 2.4%, compared with below 1% as PP-13.

Another placental protein, named PP-9 was discovered and characterized by H.Bohn et al (New soluble placental tissue proteins, Immunology of Human Placental Proteins, Placental Supplement 4, 1982, Praeger Publishers). Its isoelectric point is between 6.4 and 6.7 and its carbohydrate content is 5.5%, which are not according to the PP-13. It was found by the Inventor that the PP-9 is also not suitable for the method according to the present invention and is of no value in the prediction of occurence of pregnancy disorders.

The Inventor is not yet in a position to explain the theoretical aspects, why only the PP-13 protein is suitable for the present method, while other placental proteins are unsuitable. However such theoretical explanations are beyond the scope of the invention.

The results presented in the present specification are based on sera obtained from pregnant woman, although one may conceive to utilize also other biological fluids such as amniotic fluid and urine.

DESCRIPTION OF THE PREFERRED EMBODIMENTS

Determination by the radioimmunoassay method (RIA)

The first step of labelling the protein by radioactive iodine, is known in the art by the term radioimmunoassay. As known, this radioimmunoassay is based on the competition of a known amount of radiolabelled antigen and an unknown amounts of the unlabelled antigen, for binding sites of a constant amount of antibody. The specific particular method selected for labelling the antigen, is carried out according to the method of Marchalonis (Biochemical Journal, Volume 113, 1963) with Lactoperoxidase-$H_2O_2$. Due to the alkalinity of the mixture, some phosphate buffer saline was also added so that the mixture reached a neutral point. The use of radioactive isotopes has enabled the immune reaction to be measured and thus it is preferably utilized in the present invention, wherein the specific protein can be determined with great sensitivity.

The radioactive iodine bound by the antigen is counted, using a Gamma Counter (such as Auto Gamma ® Counter produced by Packard) and the yield thereto is calculated. The yield is calculated using the following formula:

$$Yield = \frac{\text{radioactivity measured by the peak of protein}}{\text{Total radioactivity}}$$

Figure 1:
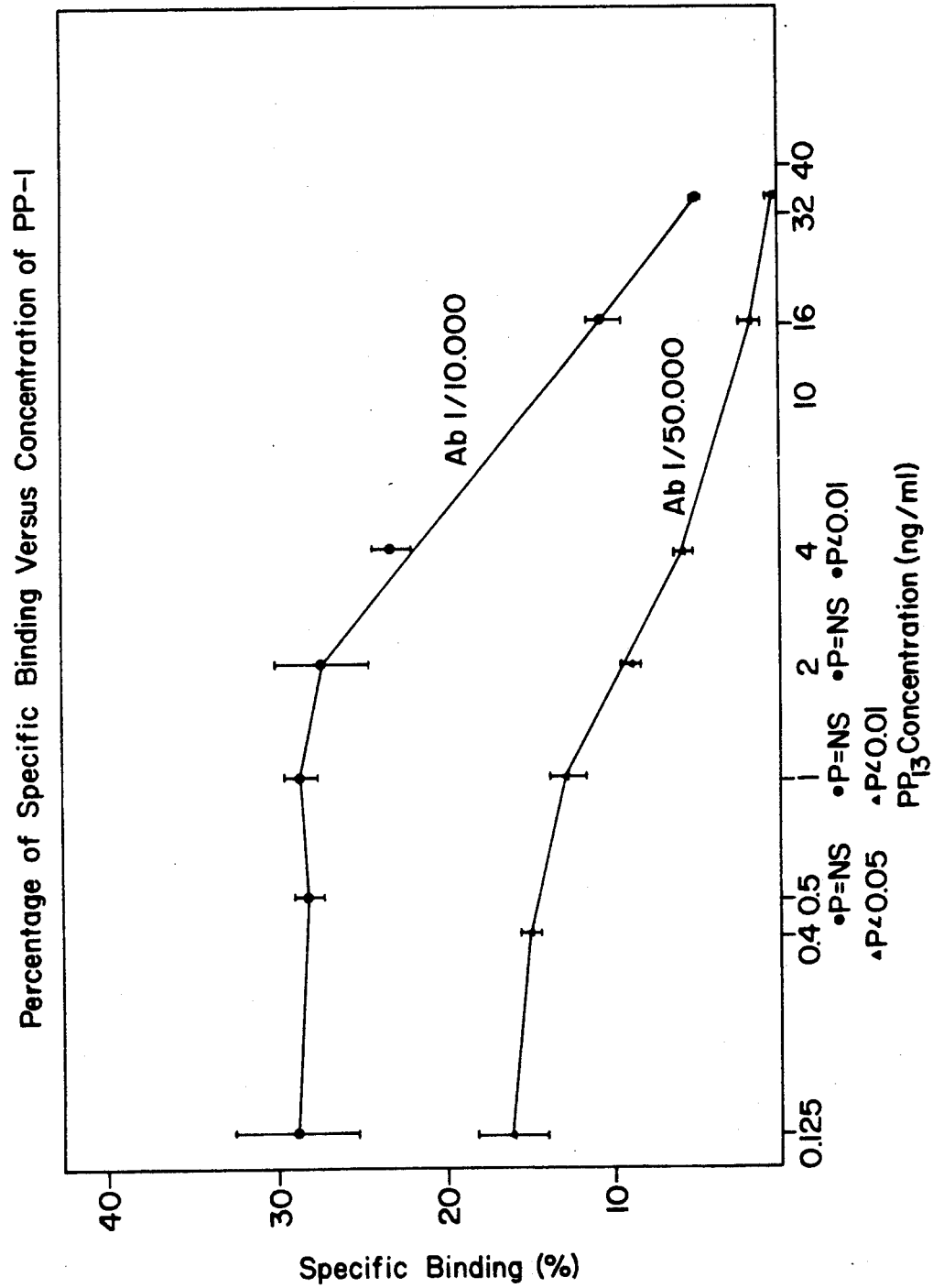
FIG. 1, presents the graphs correlating the percentage of specific binding versus the concentration of the PP-13 protein.

The most preferred concentrations of the antibody for obtaining the proper complex (AG-AB) is the dilution factor range between 1/10,000 to 1/50,000. In this range it was discovered that there is a linear correlation between the specific binding and antibody concentration. This appears in a clear manner in FIG. 1, wherein the specific binding (expressed in percentage) is given versus the concentration of the PP-13 protein. Based on the yield of the radioactive iodine, the specific activity of the labelled antigen is calculated and subsequently this is correlated with standard evaluation curves.

In the second step, the labelled antigen obtained in the first step is correlated with the biological fluid which is tested, and a first antibody. This antibody was obtained from antiserum specific against PP-13 produced in a hyperimmunized rabbit, diluted by a buffer (pH=7.4) consisting of $NaN_3$ (1 g/1) and TRIS-HCl (0.02 mol/1). In the third step, a second antibody, attached to a solid support, developed in the serum of a donkey, was admixed with the product of step (b) and the precipitated complex was separated by centrifugation and washed with a Phosphate Buffer Saline Solution.

Finally, in the fourth step, the radioactivity was determined in the washed complex by a gamma irradiation counter (Auto Gamma ® produced by Packard).

The above steps of the method will enable the following data to be obtained:

(1) The level of total radioactivity introduced in the system of the experiment.

(2) The degree of non-specific binding of the labelled antigen and the second antibody.

(3) The zero binding of the antigen and its specific antibody.

(4) Calibration of the system by utilizing a series of known concentrations of the unlabelled antigen.

Figure 2:
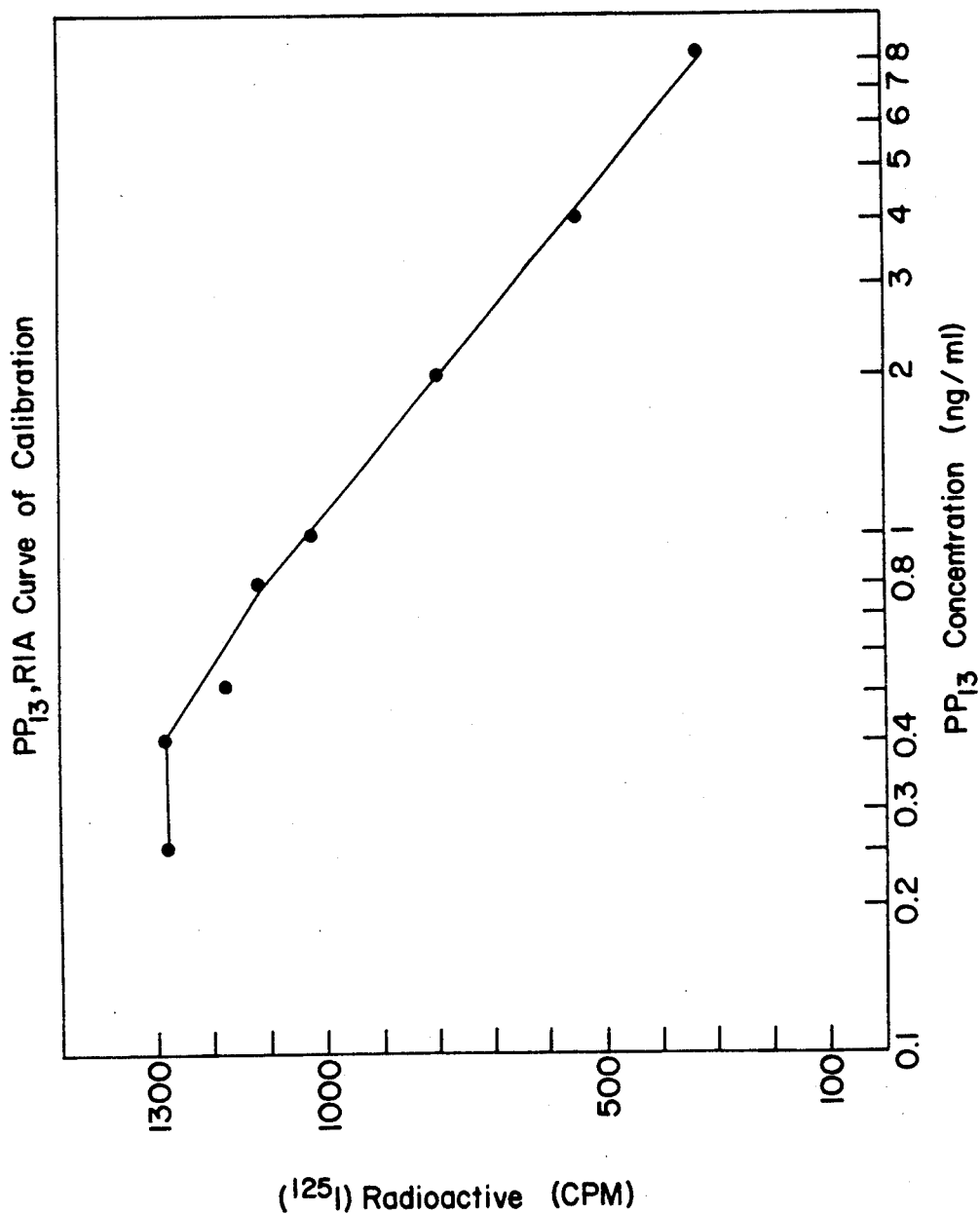
FIG. 2, presents the correlating graph of the $^{125}I$ radioactivity versus the PP-13 protein concentration.

In the attached FIG. 2, the radioimmunoassay calibration curve of the protein is shown, correlating the $^{125}I$ radioactivity (expressed in counts per minute) versus the PP-13 protein concentration (expressed in ng/ml).

Determination by the Elisa method

According to another embodiment, the PP-13 levels can be determined by a non-radioactive diagnostic method: Enzyme Linked Immuno-Sorbent Assay (ELISA). This method is more modern in current diagnostic practice so that commercial and clinical applications of the PP-13 determination are likely to employ the RIA and/or the ELISA methods.

Figure 3:
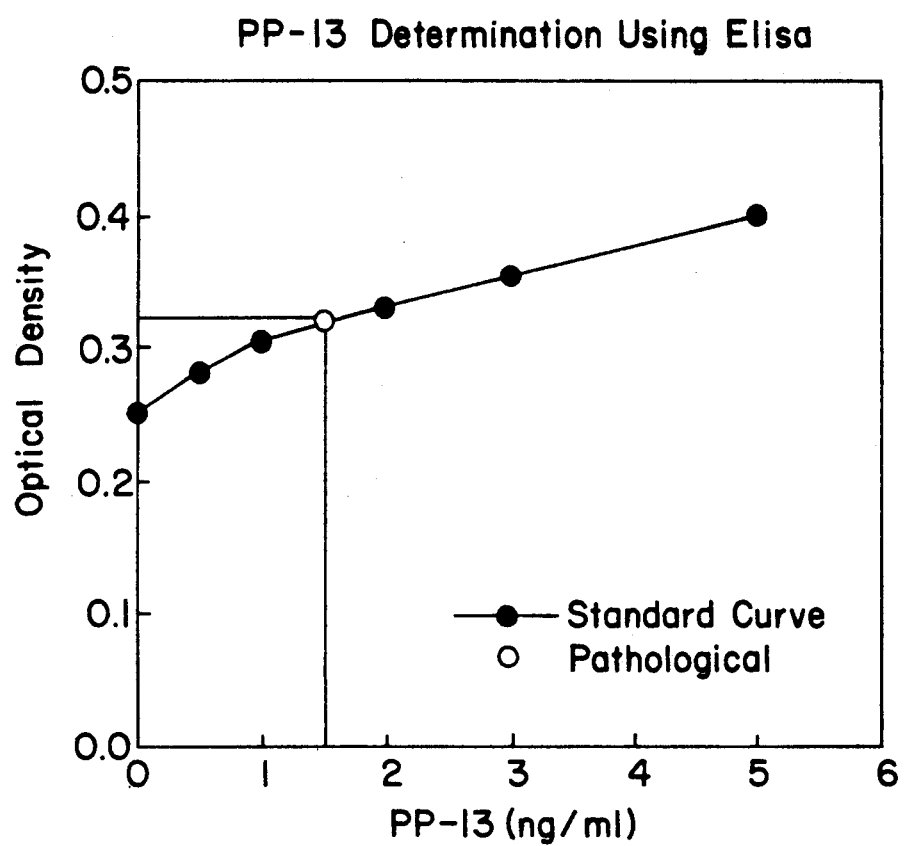
FIG. 3, presents the measurements of various known concentrations of PP-13 using the ELISA method and one serum sample from a pregnant woman.

The ELISA method is based on the adhesion of the anti PP-13 antiserum (originating from rabbits) onto the bottom of a plastic surface. The PP-13 antigen, found in maternal serum, is specifically bound by the anti-PP-13 antibodies. Washing step removes unbound entities from the assay system. A rabbit anti-PP-13 antiserum is subsequently applied. Specific antibodies are thus bound to the PP-13 antigen. In a second step of washing, the unbound non-specific rabbit serum components is removed. Following this step a molecular complex (conjugate) composed of anti-rabbit antiserum (originating in goat) covalently conjugated to the enzyme alkaline phosphatase is applied to the assay system. The specific anti-rabbit goat antibodies bind the rabbit antibodies anchored onto the PP-13 antigen. The actual quantitative determination of the PP-13 level is effected by applying the alkaline phosphatase substrate (pNPP) and measuring the optical density at 405 nm. The intensity of the optical density is quantitatively proportional to the level of PP-13 in the serum. Actual concentration of PP-13 in the serum can be accurately determined when a standard curve using known concentrations of PP-13 are employed. FIG. 3 depicts such standard curve and the determination of PP-13 levels in male and pregnant female sera. The clinical usefulness of PP-13 was demonstrated in a study composed of 888 women and 2020 blood samples. The reliability of PP-13 as a diagnostic marker was assessed for a large number of pregnancy-related diseases. The list of these diseases, the number of women possessing these diseases and the percentage of cases in each disease category are presented in the following Table I.

TABLE I

CLINICAL CATEGORIES FOR GROUPS IN WHICH THE SERUM PP-13 VALUES WERE ANALYZED.

| Disease | Number of cases | % |
| --- | --- | --- |
| Normal pregnancy | 366 | 44.2 |
| Hypertension of pregnancy | 125 | 14.9 |
| Chronic Hypertension | 45 | 5.4 |
| Severe preeclampsia | 21 | 2.5 |
| Mild preeclampsia | 17 | 2.0 |
| Gestational hypertension | 27 | 3.2 |
| Chronic Hypert. + preeclampsia | 14 | 1.7 |
| Preterm delivery | 83 | 10.0 |
| Spontaneous preterm delivery | 50 | 6.0 |
| IUGR (Brenner) | 56 | 6.7 |
| IUGR (Usner) | 21 | 2.5 |
| Diabetes (Total) | 40 | 4.8 |
| Gestational diabetes | 27 | 3.2 |
| Diabetes Type I & II | 13 | 1.6 |
| Twins | 25 | 3.0 |
| Infant's weight <p−90 | 66 | 7.9 |
| Post-term delivery | 11 | 1.3 |
| 1st trimester bleeding | 54 | 6.5 |
| 2nd & 3rd trimester bleeding | 9 | 1.1 |
| Endocrine diseases | 28 | 3.4 |
| Urinary infection | 29 | 3.5 |
| Neurologic diseases | 8 | 1.0 |
| Anemia >9 gr % | 7 | 0.8 |
| Heart disease | 10 | 1.2 |
| Smoking | 46 | 5.5 |
| Perinatal mortality | 14 | 1.7 |

The reliability of PP-13 determination as a marker for each of the diseases was quantitatively assessed by determining the sensitivity of PP-13 assay on the background of 70% specificity (the definitions of the terms: sensitivity, specificity, corrected sensitivity, positive predictive value and negative predictive value are presented in Appendix I). Statistical significance was calculated using test with Yates' correction.

It was surprisingly discovered that PP-13 assay demonstrated high sensitivity in the range of 80%-100% for three disease entities in particular: preeclampsia, IUGR and preterm delivery. High sensitivity was also noted to some extent for twin pregnancies.

The diagnostic parameters of PP-13 assay for the early detection of preeclampsia are shown in the following Table II.

TABLE II

SENSITIVITY (S) CORRECTED SENSITIVITY (CSENS), POSITIVE PREDICTIVE VALUE (PPV), NEGATIVE PREDICTIVE VALUES (NPV) AND STATISTIC VALUE (P) OF PP-13 IN CASES OF PREECLAMPSIA DURING WEEKS 24–34, AT SPECIFICITY OF 70%. CORRECTED SENSITIVITY (CSENS) REFERS TO THE SENSITIVITY IN CASES WHERE THE TIME LAG BETWEEN THE PP-13 TEST AND THE CLINICAL DIAGNOSIS OF THE PATHOLOGY WAS GREATER THAN 2 WEEKS P-VALUE WAS CALCULATED BY $X^\sim$ TEST WITH YATES'S CORRECTION.

| P-VALUE | NPV (%) | PPV (%) | CSENS (%) | S (%) | (WEEKS) |
| --- | --- | --- | --- | --- | --- |
| P. | 96 | 13 | 44 | 55 | 24–28 |
| N.S. | 95 | 12 | 44 | 55 | 26–30 |
| P<0.01 | 99 | 15 | 80 | 89 | 28–32 |
| P<0.01 | 99 | 15 | 79 | 89 | 30–34 |

The diagnostic parameters of the PP-13 assay for the early detection of Intra-Uterine Growth Retardation (IUGR) are shown in Table III.

TABLE III

SENSITIVITY, CORRECTED SENSITIVITY, POSITIVE AND NEGATIVE PREDICTIVE VALUES AND P VALUE OF PP-13 IN CASES OF INTRAUTERINE GROWTH RETARDATION (ACCORDING TO USHER), DURING WEEKS 24–34, AT SPECIFICITY OF 70% CORRECTED SENSITIVITY (CSENS) REFERS TO THE SENSITIVITY IN CASES WHERE THE TIME LAG BETWEEN THE PP-13 TEST AND THE CLINICAL DIAGNOSIS OF THE PATHOLOGY WAS GREATER THAN 2 WEEKS P-VALUE WAS CALCULATED BY $X^\sim$ TEST WITH YATES'S CORRECTION.

| P-VALUE | NPV (%) | PPV (%) | CSENS (%) | S (%) | (WEEKS) |
| --- | --- | --- | --- | --- | --- |
| P. | 98 | 6 | 67 | 60 | 24–28 |
| P<0.01 | 97 | 15 | 67 | 73 | 26–30 |
| P<0.01 | 97 | 13 | 71 | 82 | 28–32 |
| P<0.01 | 100 | 12 | 100 | 100 | 30–34 |

The diagnostic parameters of the PP-13 assay for the early detection of preterm delivery are shown in Table IV.

TABLE IV

SENSITIVITY, CORRECTED SENSITIVITY POSITIVE AND NEGATIVE PREDICTIVE VALUES AND P VALUE OF PP-13 IN CASES OF SPONTANEOUS PRETERM DELIVERY DURING WEEKS 24–34, AT SPECIFICITY OF 70%. CORRECTED SENSITIVITY (CSENS) REFERS TO THE SENSITIVITY IN CASES WHERE THE TIME LAG BETWEEN THE PP-13 TEST AND THE CLINICAL DIAGNOSIS OF THE PATHOLOGY WAS GREATER THAN 2 WEEKS P-VALUE WAS CALCULATED BY $X^\sim$ TEST WITH YATES'S CORRECTION.

| P-VALUE | NPV (%) | PPV (%) | CSENS (%) | S (%) | (WEEKS) |
| --- | --- | --- | --- | --- | --- |
| P. | 89 | 17 | 40 | 40 | 24–28 |
| P. | 89 | 17 | 39 | 39 | 26–30 |
| P<0.01 | 95 | 20 | 67 | 69 | 28–32 |
| P<0.01 | 99 | 17 | 100 | 90 | 30–34 |

In all the disease entities, the reliability of the PP-13 assay as evidenced by the level of statistical significance increases with gestational age.

It should be strongly emphasized that PP-13 values are not a direct and predictable reflection of placental damage. As found, pregnancy states which are not accompanied by placental damage were shown to manifest PP-13 levels with remarkably high sensitivity. As an example of such a case, it was discovered that 88% of twin pregnancies, which were otherwise completely normal pregnancies, which were otherwise completely normal pregnancies with no clinical symptoms, had PP-13 values higher than normal (sensitivity of 88%).

In addition, in a large proportion of IUGR cases, as evidenced, PP-13 was found to be abnormally lower than the confidence limits defining sensitivity of 70%, whereas other cases of the same pathology had higher PP-13 values than these limits.

There is currently no agreement in the professional community as to the exact causes for the three pathologies for which PP-13 was shown to serve as a reliable marker. Factors such as hypertension, bacterial infections, diabetes, genetic aberations, teratogenic compound and many others can lead to one or a combination of the three pathologies. These considerations as well as the observastions that PP-13 can be either lower or higher than normal, or increased in a normal pregnancy, are clear indications that PP-13 values can by no means be considered to reflect placental intactness. Therefore, PP-13 can serve to reliably identify the appearance of preeclampsia, IUGR or preterm delivery, before their clinical manifestations can be detected by current diagnostic means.

While the invention will be hereafter described in a detailed manner with certain preferred embodiments and compositions, it will be understood that it is not intended to limit the invention to these particular embodiments. On the contrary, it is intended to cover other alternatives, modifications or other ingredients as may be included within the scope of the invention as defined by the appended Claims. It should be understood that the particulars are by way of example and for purposes of illustrative discussion of the procedure for carrying out the method according to the present invention, without being limited thereto. The reagents utilized in the following Examples and the source are as follows:

Protein PP-13, produced by Behringwerke Aktiengesellschaft, Lot No. 211/233.

Anti PP-13, antiserum, Lot No. 160 Z B.

Radioactive iodine (125I) produced by Israel Nuclear Center in a solution of Sodium hydroxide (pH=8-11) possessing a specific activity of 15-20 uci/ug.

Lactoperoxidase, produced by sigma (St.Louis, Missouri) Lot No. 2005.

Hydrogen Peroxide, 30% concentration, produced by Sigma Lot No. H-1009.

The instruments utilized for the measurements were as 1 follows:

Gamma Counter, produced by Elscint, Israel (Integrated Nuclear Spectrometer, model INS-llN).

Auto Gamma R400 (GD, produced by Packard (U.S.A.).

Cooled Ultra Centrifuge, produced by Cryofuge, Heraeus, West-Germany.

Column Sephadex RG-100 (9 x 550 mm).

Fraction Collector, produced by Pharmacia, Frac-100 (Sweden).

EXAMPLE 1

STEP A

The labelling was done by radioactive iodine (125I), at room temperature in a 2 ml plastic test tube, having at its bottom a metal rod operated by a magnetic stirrer, which rotates at 2 rotations per second. The following reagents were introduced:

3 $\mu$g of placental protein in 10 $\mu$l of phosphate buffer saline (pH=7.2);

1 $\mu$g of lactoperoxidose in 6 $\mu$l of phosphate buffer saline;

325-350 $\mu$ci of $^{125}$I in 2 $\mu$l of NaOH (pH=8-11); and 9 nmole of hydrogen peroxide in 10$\mu$l of phosphate buffer saline.

The reaction solution consisted of 5 $\mu$g of PP-13 to which 1 $\mu$g of lactoperoxidase and 325 $\mu$ci of $^{125}$I were added. Due to the relatively high alkalinity 3 ul of phosphate buffer solution (0.4 M) was added, the pH reaching a neutral value. The iodination reaction started by the addition of hydrogen peroxide and continued for about 3 minutes. The iodination was stopped by adding 300 ul of a solution consisting of:

phosphate buffer saline containing 10 g/l of bovine serum albumen; NaI (2 g/1); NaN (1 g/1) and NaCl (8.5 g/1). After an additional stirring for 1 minute, the mixture was passed over a Sephadex RG-100 column for extracting the labelled protein from the free iodine and the other reagents, by a solution consisting of: phosphate buffer saline +1% bovine serum albumen and 0.1% NaN3. From the resulting fractions the extent of iodination was determined by a Gamma Counter (Elscint) and the calculated yield was found to be 64.6%.

In order to calculate the specific activity of the labelled antigen, samples of 10 ul were taken and again counted by Packard Gamma Counter and found to be 86178 cpm/ng.

STEP B.

Standard solutions of various concentrations in the range of 0.2 ng/ml to 64 ng/ml of antigen in a buffer (tris HC1, pH=7.4, 0.02 m/l and NaN3, 1 g/1) were prepared. The labelled antigen consisted of a diluted solution of 1 ng/ml. The first antibody was the antiserum of the placental antigen diluted in a buffer (with the same composition as above).

STEP C

The second antibody, was developed in the serum of a donkey. The test was carried out in a plastic test tube the working scheme being described in the following Table 2.

TABLE 2

The working scheme for the determination of placental anitgen in the human serum using radioimmunoassay.

| Kind of incubate | Buffer A: Tris-HCl, pH = 7.4 (0.02 m/l) + NaN3 (1 g/l) $\mu$l | Standards $\mu$l | Sample $\mu$l | Tracer antigen $\mu$l | 1st antibody $\mu$l | 2nd antibody $\mu$l |
|---|---|---|---|---|---|---|
| Total Radio-activity | 200 | — | — | 100 | — | — |
| Nonspecific | 200 | — | — | 100 | — | 500 |
| Zero binding | 100 | — | — | 100 | 100 | 500 |
| Standards | — | 100 | — | 100 | 100 | 500 |

TABLE 2-continued

| Kind of incubate | Buffer A: Tris-HCl, pH = 7.4 (0.02 m/l) + NaN$_3$ (1 g/l) μl | Standards μl | Sample μl | Tracer antigen μl | 1st anti- body μl | 2nd anti- body μl |
|---|---|---|---|---|---|---|
| Samples | — | — | 100 | 100 | 100 | 500 |

The working scheme for the determination of placental anitgen in the human serum using radioimmunoassay.

The reactions between the labelled antigen with the sample of serum or respective standards were carried out for about 18 hours, followed by the addition of the second antibody and agitation for about 10 minutes. The mixtures were centrifuged at room temperature for 30 minutes (at 1000×G) and the precipitates washed with 500 ul of phosphate buffer saline and again centrifuged. The radioactivity in the washed precipitate was determined by Packard Gamma Counter. The results obtained are summarized in the attached FIG. 1. It clearly appears from said FIGURE that an antibody (Ab) with a concentration of 1/50000, gave an adequate binding range for an antigen concentration of between 0.4-32 ng/ml.

In order to calculate the antigen concentrations in the samples tested, a calibration curve was prepared (shown in FIG. 2) correlating the radioactivity of $^{125}$I (expressed in counts per minute) versus the PP-13 concentration (expressed in ng/ml).

APPENDIX I

Considering the fact that PP-13 assay is to be used as a diagnostic tool, the analytical model appropriate for such assay employs the following diagnostic parameters: "sensitivity", "specificity" and "predicative value". These parameters can be examplified by the biochemical test employed for early detection of newborns whose weight is below the 10$^{th}$ percentile (IUGR) (Table 2).

TABLE 1

STATISTICAL PRECITORS USED IN THE INTERPRETATION OF A TEST RESULT.

| | NORMAL BIRTH WEIGHT | IUGR |
|---|---|---|
| TEST RESULT POSITIVE | FALSE POSITIVE (FP) | TRUE POSITIVE (TP) |
| TEST RESULT NEGATIVE | TRUE NEGATIVE (TN) | FALSE NEGATIVE (FN) |

True Positive - abnormal result for a woman with IUGR.
True Negative - normal result for a normal woman.
False Negative - abnormal result for a normal woman.
False Negative - normal result for a woman with IUGR.
Sensitivity:
Accuracy of the test in correctly identifying newborn with IUGR.
Sensitivity = [TP/(TP + FN)].
Specificity:
Accuracy of the test in correctly identifying normal weight.
Sensitivity = [TN/TN + FP].
Positive predictive value (PPV):
Accuracy of the test in identifying IUGR when test result is positive.
PPV = [TP/(TP + FP)].
Negative predictive value (NPV):
Accuracy of the test in identifying normal newborn when test result is negative.
NPV = [TN/(TN + FN)].
Relative risk:
The ratio between the probability of delivering an infant with IUGR when test result is positive and test result is negative.
Relative risk = [TP/(TP + FP) : FP/FN + FN)].

Claims

1. A method of early screening for high risk pregnancy, comprising the steps of:
   (a) providing a serum sample from a pregnant woman in her 26th to 34th week of gestation;
   (b) determining the level of the human placental protein, PP-13, in said sample; and
   (c) comparing said level with normal levels for women with the same gestational age; with a statistically significant deviation from normal levels being strongly indicative of a pregnancy-related disorder selected from the group consisting of pre-eclampsia, intrauterine growth retardation and preterm delivery.

2. The method according to claim 1, wherein the PP-13 is determined by radioimmunoassay.

3. The method according to claim 2, wherein said radioimmunoassay comprises the steps of:
   (a) incubating said serum sample from a pregnant woman with labelled PP-13 antigen and a first antibody which specifically binds said antigen;
   (b) reacting the product obtained in step (a) with a second antibody to precipitate a complex; and (c) determining the radioactivity in said complex and relating the radioactivity to the amount of antigen in the serum sample.

4. The method according to claim 3, wherein the level of said antigen is above 0.71 n/ml.

5. The method according to claim 3, wherein said first antibody is obtained from antiserum raised against said antigen in an animal.

6. The method according to claim 5, wherein said concentration of the first antibody, for obtaining the proper complex AG-AB, is between 1/10,000 to 1/50,000.

7. The method according to claim 1, wherein the PP-13 is determined by the ELISA method.

8. The method according to claim 7, wherein an anti-PP-13 antibody is adhered onto the bottom of a plastic surface, the PP-13 antigen found in said serum sample being specifically bound by the anti-PP-13 antibody.

9. The method according to claim 8, wherein a probe antibody is labeled with alkaline phosphatase, and the quantitative determination of the PP-13 level is carried out by applying an alkaline phosphatase substrate and measuring the optical density at 405 nm.

10. The method according to claim 11, wherein said level of PP-13 is determined with a background of 70% specificity for a four-week gestational period including the gestational age of the woman being screened.

11. The method of claim 10, wherein the sensitivity is 80–100%.

12. The method according to claim 1, wherein said serum sample is taken from a woman in her 28th to 34th week of gestation/

13. The method according to claim 12, wherein said woman is in her 30th to 34th week of gestation.

* * * * *